United States Patent [19]
Mukai et al.

[11] Patent Number: 5,021,339
[45] Date of Patent: Jun. 4, 1991

[54] YEAST PROMOTER TRUNCATED GAP-DH

[75] Inventors: Hiromichi Mukai; Hajime Horii; Muneo Tsujikawa; Haruhide Kawabe; Hirofumi Arimura, all of Osaka; Tadakazu Suyama, Kyoto, all of Japan

[73] Assignee: Green Cross Corporation, Osaka, Japan

[21] Appl. No.: 397,347

[22] Filed: Aug. 24, 1989

Related U.S. Application Data

[63] Continuation of Ser. No. 914,979, Oct. 3, 1986, abandoned.

[30] Foreign Application Priority Data

Oct. 3, 1985 [JP] Japan .................................. 60-219191
Feb. 4, 1986 [JP] Japan .................................. 61-21198

[51] Int. Cl.$^5$ .......................... C07H 15/12; C12N 1/00; C12P 19/31
[52] U.S. Cl. ..................................... 435/69.1; 435/91; 435/172.3; 435/320.1; 435/255; 435/256; 536/27; 935/37
[58] Field of Search ..................... 435/64.1, 69.2, 69.3, 435/172.3, 320, 91, 320.1; 536/27; 935/37

[56] References Cited

U.S. PATENT DOCUMENTS 4,618,578 10/1986 Burke et al. ........................... 435/68
4,722,840 2/1988 Valenzuela et al. .................. 424/88

FOREIGN PATENT DOCUMENTS 0120551 10/1984 European Pat. Off. .......... 435/69.1
0164556 12/1985 European Pat. Off. .......... 435/69.1

OTHER PUBLICATIONS

Bitter, G. A. et al., Expression of Heterologous Genes in S. cerevisiae from Vectors Utilizing the Glyceraldehyde-3-Phosphate Dehydrogenase Gene Promoter; Gene 32 (1984), pp. 263–274.
Völker, T. A. et al; Deletion Analysis of a Bacteriophage T$_4$ Late Promoter; Gene 33 (1984), pp. 207–213.
Holland, G. P. et al; Homologous Nucleotide Sequences at the 5' Termini of Messenger RNAs Synthesized from the Yeast Enolase and Glyceradehyde-3-Phosphate Dehydrogenese Gene Families; J. Biol. Chem. 258 (1983), pp. 5291–5299.
Cell, vol. 37, pp. 629–633, Feb. 1984.

Primary Examiner—Robin L. Teskin
Attorney, Agent, or Firm—Sughrue, Mion, Zinn, Macpeak & Seas

[57] ABSTRACT

A DNA sequence of the yeast glyceraldehyde-3-phosphate dehydrogenase (GAP-DH) promoter and a process for preparing a heterologous protein utilizing said DNA sequence as a promoter are disclosed, said GAP-DH promoter comprising a region upstream of an initiator codon of the GAP-DH protein up to −164 bp as a minimum unit. Since the GAP-DH promoter is small in size, a physiologically active substance can be expressed in yeasts effectively and recombination of DNA can be simplified.

6 Claims, 5 Drawing Sheets

FIG. 1

```
-150
TATTCCCTACTGACTAATAAGTATATAAAGACGGGTAGGTATTGATTGTAATTCTGTAAATCT
                                                              -101
-100                                               -50
ATTTCTTAAACTTCTTAAATTCTACTTTTATAGTTAGTCTTTTTTTAGTTTTAAAACACCAAGAACTTAGTTTCG
```

GAP-DH gene
… GAP-DH promoter
… DNA fragment of GAP-DH promoter
… terminator of GAP-DH gene
… DNA fragment containing 4
… 1.3 kb DNA fragment containing HBsAg gene
… HBsAg gene

YEAST PROMOTER TRUNCATED GAP-DH

This is a continuation of application Ser. No. 06/914,979, filed Oct. 3, 1986 now abandoned.

FIELD OF THE INVENTION

This invention relates to an improved yeast promoter.

BACKGROUND OF THE INVENTION

Expression of heterologous genes such as B type hepatitis virus surface antigen or HBsAg, IFN-α, etc. in yeast has been carried out. It is known that the mechanism of control on the yeast promoter is generally a positive control. In connection with this positive control, the existence of an upstream activation site (UAS), which is located several hundreds bases upstream of the initiation point of translation and which functions in a cis-sequence, has been suggested as a controlling factor of the promoter, (see L. Guarente, Cell, 36, 799 (1984)). It has been found that replacement of the UAS with a different UAS releases the promoter from its normal control system. That is, the promoter comes under the control of the new UAS (see L. Guarente et al., Proc. Natl. Acad. Sci., USA, 79, 7410 (1982), L. Guarante et al., Cell, 36, 503 (1984), K. Struhl, Proc. Natl. Acad. Sci., 81, 7865 (1984).

Yeast promoters include the glyceraldehyde-3phosphate dehydrogenase (GAP-DH) promoter, which is utilized for a plasmid producing B type hepatitis virus surface antigen (HBsAg). For example, Bittler, G. A. & Egan, K. M., Gene, 32, 263–274 (1984) describes the expression of heterologous genes in Saccharomyces cerevisiae from an expression vector utilizing the GAP-DH gene promoter, and EP-A-120,551 corresponding to JP-A-210888/84 describes a yeast expression vector and a method of its use.

For example, as described in Reference Example 1 below, the HBsAg-producing plasmid pGG5 was constructed using the GAP-DH promoter, the HBsAg structural gene, the GAP-DH terminator, a replication initiator point of E. coli, marker genes (e.g., the ampicillin-resistant gene (Apc) in E. coli and the leucine gene in yeast) and a replication initiator point in yeast.

SUMMARY OF THE INVENTION

It has been found in the present invention that the promoter activity of the GAP-DH promoter can be maintained even if the region above the restriction enzyme site XmnI (−164), which is about 25 bp upstream of TATA box, is deleted.

The present invention relates to a DNA sequence in the region from the initiator codon of the yeast GAP-DH protein up to −164 bp in the yeast GAP-DH promoter and a promoter.

BRIEF DESCRIPTION OF THE DRAWINGS

FIG. 1 shows the nucleotide base sequence of the GAP-DH small-sized promoter (from −24 to −164 bp) of the present invention.

Figure 2A:
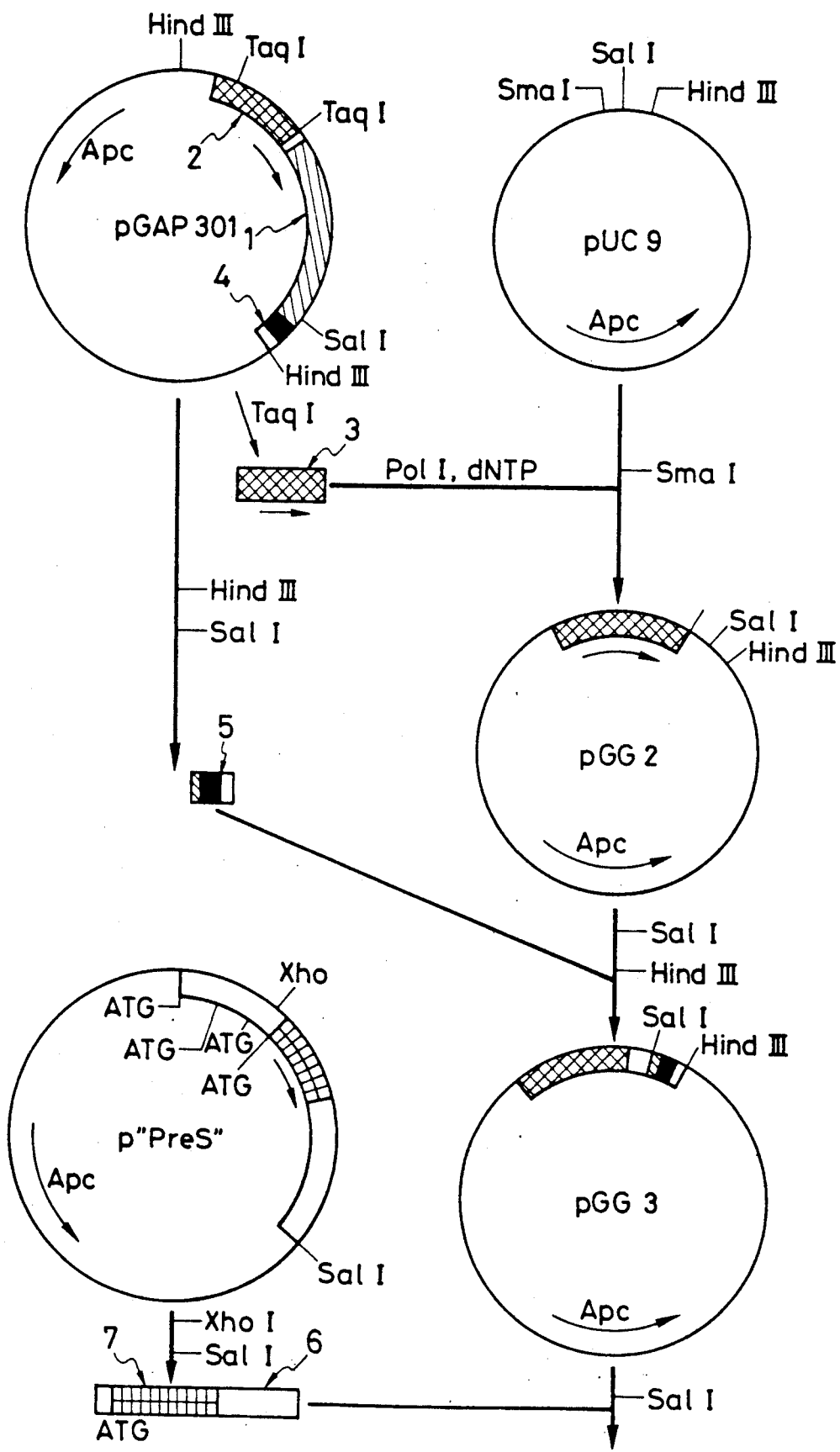
FIGS. 2(a) and 2(b) illustrate the preparation of plasmid pGG5 carrying thereon the GAP-DH promoter.

In these figures, the numerals 1 to 7 have the following meanings:

1 … GAP-DH gene
2 … GAP-DH promoter
3 … DNA fragment of GAP-DH promoter
4 … terminator of GAP-DH gene
5 … DNA fragment containing 4
6 … 1.3 kb DNA fragment containing HBsAg gene
7 … HBsAg gene

DETAILED DESCRIPTION OF THE INVENTION

The GAP-DH promoter which can be used in this invention is known, and its base sequence has been disclosed in EP-A-120,551. Therefore, the starting material to be improved can easily be prepared in a known manner, for example, from chromosomal DNA of yeast as shown in Reference Example 1 hereinafter given.

The GAP-DH promoter gene as isolated or contained in a plasmid can be cleaved by a specific restriction enzyme to effect deletion treatment. Deletion can be carried out upstream of an initiator codon of the GAP-DH protein, and preferably in the vicinity of −164 bp. Suitable restriction enzymes which can be employed include XmnI. The GAP-DH promoter gene is further cleaved upstream of the initiator codon in the vicinity of −25 bp with the restriction enzyme to complete the deletion treatment.

The DNA sequence of the thus small-sized promoter can be determined in accordance with the method of Maxam-Gilbert to obtain a base sequence as shown in FIG. 1. This base sequence is equal to the known one but is much smaller in size.

The small-sized GAP-DH promoter is then inserted into a plasmid and repaired by treating with known restriction enzymes and ligases.

A gene which encodes a useful physiologically active substance can then be inserted downstream of the thus small-sized GAP-DH promoter to obtain a recombinant plasmid.

Yeast can then be transformed using the recombined plasmid and then allowed to express the cloned gene product to thereby effectively produce a desired protein.

Various techniques, reactions and methods of analyses which can be employed in the present invention are known in the art. All the enzymes to be used in the present invention are commercially available unless otherwise indicated. For example, they can be obtained from Takara Shuzo Co., Ltd., New England Biolabs (NEB), Mass., U.S.A., Amersham, G. B., Bethesda Research Laboratories (BRL), Md., U.S.A., etc.

With respect to buffer solutions and reaction conditions for enzymatic reactions to be used in this reaction, the recommendations by the respective maker are followed unless otherwise indicated.

Transfection of E. coli by using a phage, transfection of E. coli by using a plasmid, plaque hybridization, electrophoresis and recovery of DNA from a gel can be carried out in accordance with the methods described in Molecular Cloning, Cold Spring Harbor Laboratory (1982). Transformation of yeast can be carried out by the method described in Method in Yeast Genetics, Cold Spring Harbor Laboratory (1981).

The small-sized GAP-DH promoter according to the present invention makes it possible to effectively express a physiologically active substance such as HBsAg, various interferons, thromboplastin activator, urokinase, etc. in yeast. Use of such a small-sized GAP-DH promoter simplifies the recombination operation of DNA. Further, the promoter of this invention, because it has a reduced size, can advantageously be used to prepare hybrid promotors so as to construct a strong expression promoter system. In addition, it is expected that the promoter of this invention maintains promoter activity even in an acetic acid medium.

The present invention will now be illustrated in greater detail by way of Reference Examples and Examples, but they are not intended to limit the scope of the present invention.

REFERENCE EXAMPLE 1

Cloning of Yeast GAP-DH Gene

DNA having a yeast GAP-DH gene sequence was prepared from yeast chromosomal DNA as follows:

Chromosomal DNA was prepared from *Saccharomyces cerevisiae*, GRF18 (leu, trp, his, met) (J. Oberto & J. Davison, *Gene*, 40, 57–65 (1985)) according to the method of D. R. Cryer, et al., *Method in Cell Biology*, 18, Chap. 3, P39, Academic Press, New York (1975).

20 μg of the resulting chromosomal DNA was completely digested with 10 units (U) of a restriction enzyme, HindIII (produced by Takara Shuzo Co., Ltd., hereinafter the same) and then ligated to 1 μg of a lambda phage, charon 28 (b1007, KH54, N1N5) DNA (commercially available under Chiron catalogue No. 53525A, BRL) which had been completely digested with 1U of HindIII. The ligation was carried out by the use of T4 DNA ligase (produced by Takara Shuzo Co., Ltd., hereinafter the same) in the manner as recommended, i.e., by reacting overnight at 16° C. The same method was applied to ligation of all of the DNA hereinafter described. After the ligated DNA was packaged by using an in vitro packaging kit (produced by Amersham) in the manner as recommended by Amersham, *E. coli*, LE392 strain (F−, hsd R514 ($r_K^-$, $m_K^-$), sup E44, lac Y1, gal K2, gal T22, met B1, trp 1255, λ−) (*Molecular Cloning* Cold Spring Harbor Laboratory (1982) p.504) was infected with the DNA according to the above-described method of molecular cloning to thereby obtain 40,000 plaques.

After the resulting 40,000 plaques were fixed to a nitrocellulose filter, they were hybridized with synthetic DNA having a DNA sequence (AACGGTTTCGGTAGA) which is the same as that of a portion contained in GAP-DH gene described in *J. Biological Chemistry*, 254, 19, 9839–9845 (1979), labelled with $^{32}P$, to perform screening according to the above-described molecular cloning method (plaque hybridization method). As a result, two highly hybridized phages being consistent in restriction enzyme mapping were obtained.

10 μg of the resulting phage DNA was completely digested with 2U of HindIII to prepare a DNA fragment derived from the 2.1 kb yeast chromosome. The DNA after complete digestion with HindIII was subjected to electrophoresis using low-gelling-temperature agarose (produced by BRL), and the 2.1 kb DNA fragment thus cut out was heat-treated at 65° C. for 10 minutes and extracted with phenol, followed by ethanol precipitation of the aqueous layer in accordance with the recommendation of BRL. This method was applied to the recovery of all of the DNA fragments hereinafter described.

1 μg of the resulting 2.1 kb HindIII DNA fragment was ligated with 1 μg of pBR322 DNA, a typical plasmid of *E. coli*, which had been completely digested with 1U of HindIII, by using 5U of T4 DNA ligase. Then *E. coli*, HB101 strain (F−, hsd S20 ($r_B^-$, $m_B^-$), rec A13, ara −14, pro A2, lac Y1, gal K2, rps L20 (Sm$^r$), xyl-5, mtl -1, sup E44, λ−) (*Molecular Cloning* Cold Spring Harbor Laboratory (1982) p.504) was transfected with the plasmid according to the above-described molecular cloning method to carry out recloning. The plasmid thus obtained by recloning was designated as pGAP301.

REFERENCE EXAMPLE 2

Preparation of Vector for HBsAq Expression

Figure 2B:
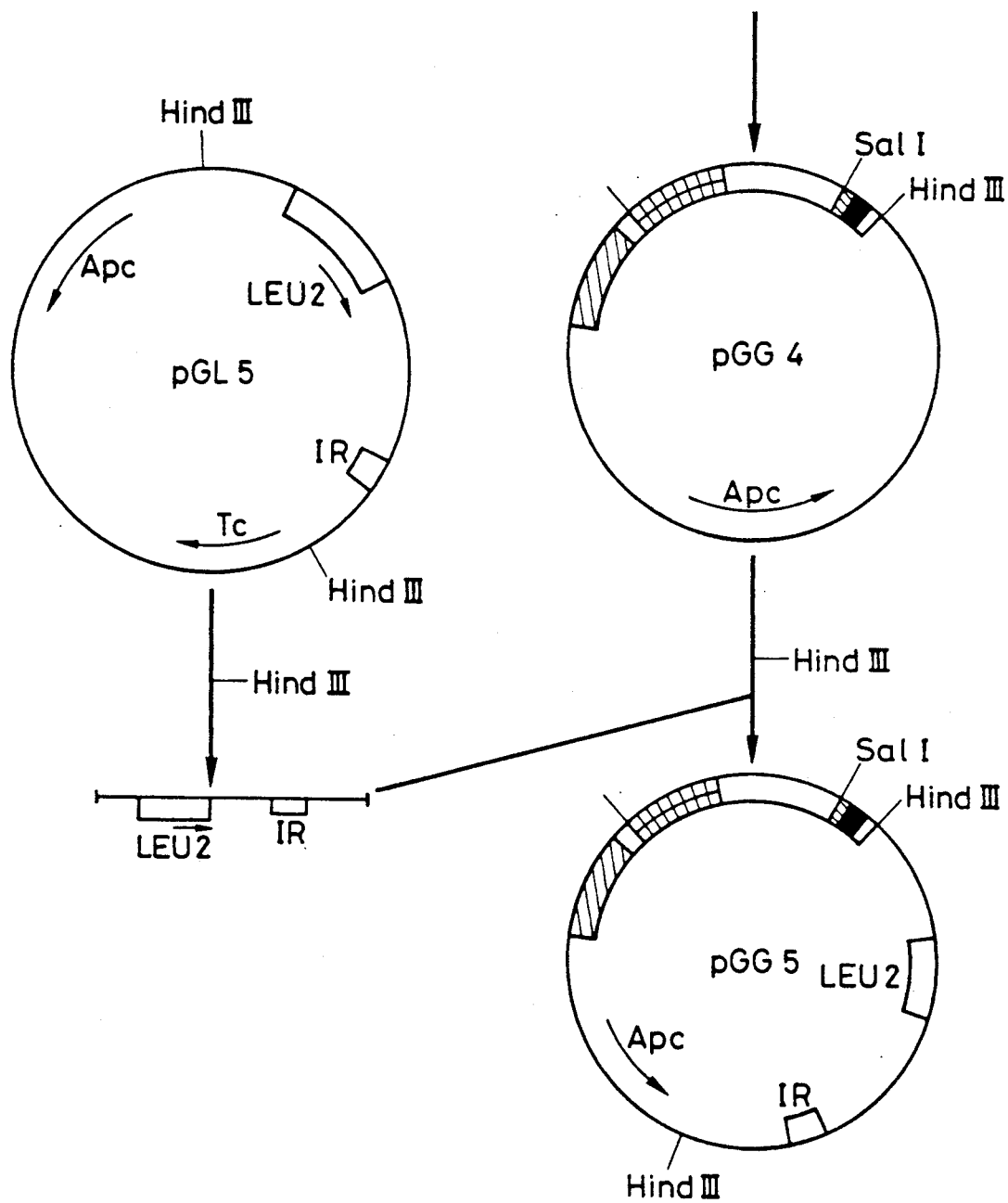
Figure 3:
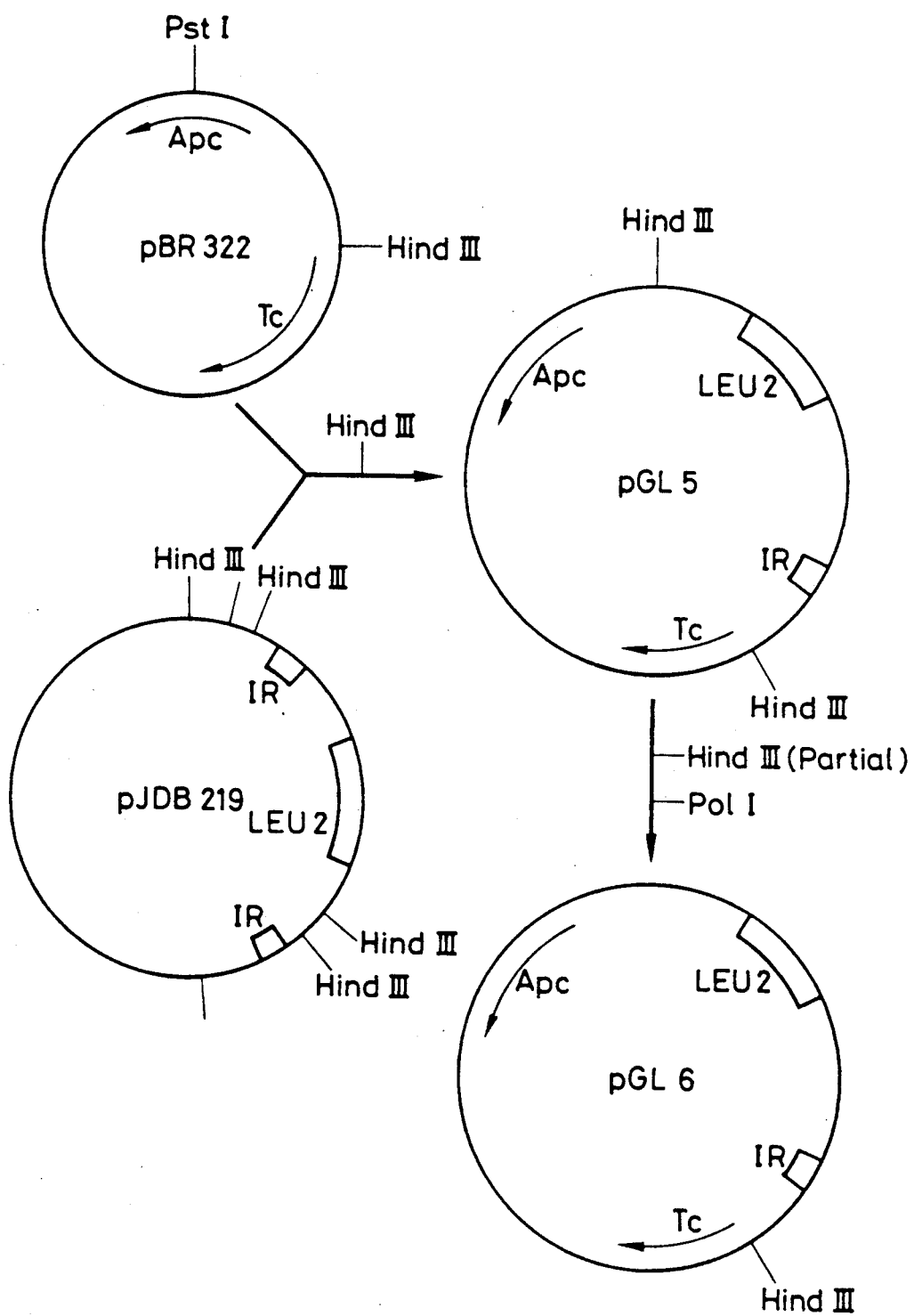
FIG. 3 illustrates the preparation of pGL5 and pGL6.

Plasmid vector pGG5 which employs the GAP-DH promoter for expression of HBsAg (B type hepatitis virus surface antigen) in yeast was constructed as shown in FIGS. 2 and 3. The description will be given referring to these figures.

4 μg of pGAP301 DNA was completely digested with 1U of TaqI (produced by NEB) and subjected to electrophoresis to thereby recover DNA fragment 3 of GAP-DH promoter 2 having a length of 652 bp from −676 to −29 taking the base at the initiator point of GAP-DH gene 1 as +1.

The resulting DNA fragment 3 was treated with 1U of DNA polymerase (PolI) (Produced by Takara Shuzo Co., Ltd.) and 0.1 μg of dNTP (deoxy NTP) to make the adhesive terminals smooth.

The DNA fragment and 1 μg of pUC9 having been completely digested with 1U of SmaI (produced by Takara Shuzo Co., Ltd.) were ligated to each other in the direction shown in the figure by means of 5U of T4 DNA ligase. *E. coli*, HB101 was transfected with this DNA. The resulting plasmid was designated as pGG2.

Then, 10 μg of pGAP301 was completely digested with 3U of SalI (produced by Takara Shuzo Co., Ltd.) and 3 U of HindIII, followed by separation by electrophoresis to prepare a 140 bp DNA fragment 5 containing terminator sequence 4 of GAP-DH gene. Further, 1 μg of pGG2 DNA was digested with 1U of SalI and 1U of HindIII, followed by electrophoresis to prepare a 3.4 kb DNA fragment. The resulting 3.4 kb DNA fragment and 140 bp DNA fragment were connected to each other using 5U of T4 DNA ligase, and the resulting plasmid was designated as pGG3.

4 μg of p"PreS" DNA was completely digested with 1U of XhoI (produced by Takara Shuzo Co., Ltd.) and 1U of SalI, followed by electrophoresis to prepare a 1.3 kb DNA fragment 6 containing HBsAg gene 7. A DNA fragment obtained by complete digestion of 1 μg of pGG3 DNA with SalI and the 1.3 kb fragment containing HBsAg were ligated to each other using 5U of T4 DNA ligase. The resulting plasmid was designated as pGG4 (FIG. 2-B).

Then, 10 μg of pGAP301 was completely digested with 3U of SalI (produced by Takara Shuzo Co., Ltd.) and 3U of HindIII, followed by separation by electrophoresis to prepare a 140 bp DNA fragment 5 containing terminator sequence 4 of GAP-DH gene. Further, 1 μg of pGG2 DNA was digested with 1U of SalI and 1U of HindIII, followed by electrophoresis to prepare a 3.4 kb DNA fragment. The resulting 3.4 kb DNA fragment and 140 bp DNA fragment were ligated to each other using 5U of T4 DNA ligase, and the resulting plasmid was designated as pGG3.

4 μg of p"PreS" DNA (offered by Biogen S. A. : FIG. 2(A)) was completely digested with 1U of XhoI (produced by Takara Shuzo Co., Ltd.) and 1U of SalI, followed by electrophoresis to prepare a 1.3 kb DNA fragment 6 containing HBsAg gene 7. A DNA fragment obtained by complete digestion of 1 μg of pGG3 DNA with SalI and the 1.3 kb fragment containing HBsAg were ligated to each other using 5U of T4 DNA ligase. The resulting plasmid was designated as pGG4 (FIG. 2-B).

In order to express HBsAg gene in yeast, it is desirable that HBsAg exists on DNA capable of self-reproduction within yeast. However, pGG4 is not capable of self-reduplication in yeast. Therefore, 5 μg of E. coli-yeast shuttle vector pJDB219 (J. D. Beggs, Nature, 275, 104) DNA was used, and was completely digested with HindIII to prepare 3.2 kb DNA fragment. 1 μg of E. coli plasmid pBR322 DNA was completely digested with HindIII and ligated with the 3.2 kb DNA fragment using 5U of T4 DNA ligase to thereby obtain shuttle vector pGL5 having two HindIII sites. One of the HindIII sites of pGL5 was changed to a smooth terminal using DNA polymerase (produced by Takara Shuzo Co., Ltd.) according to the method described in Molecular Cloning Cold Spring Harbor Laboratory (1982) p.113 to thereby prepare plasmid pGL6 having one HindIII site (FIG. 3).

pGL5 had a replication initiator point derived from yeast 2 μ-DNA and LEU2 gene, a marker gene of yeast, on the 3.2 kb HindIII DNA fragment and a replication initiator point of E. coli and tetracyclin-resistant gene (Tc), a marker gene of E. coli, on another DNA fragment. In order to obtain a yeast replication initiator point and LEU2 gene, 2 μg of pGL5 DNA was completely digested with 1U of HindIII, followed by electrophoresis to prepare a 3.2 kb fragment. 1 μg of pGG4 DNA was completely digested with 1U of HindIII and then ligated with the 3.2 kb DNA fragment using 5U of T4 DNA ligase to prepare plasmid pGG5 (FIG. 2-B). There was thus obtained vector pGG5 for producing HBsAg in yeast which contained a promoter region having a sufficient length (652 bp) of the GAP-DH promoter. HBsAg gene and GAP-DH terminator (FIG. 2-B).

EXAMPLE

Digestion of GAP-DH Promoter Region

Figure 4:
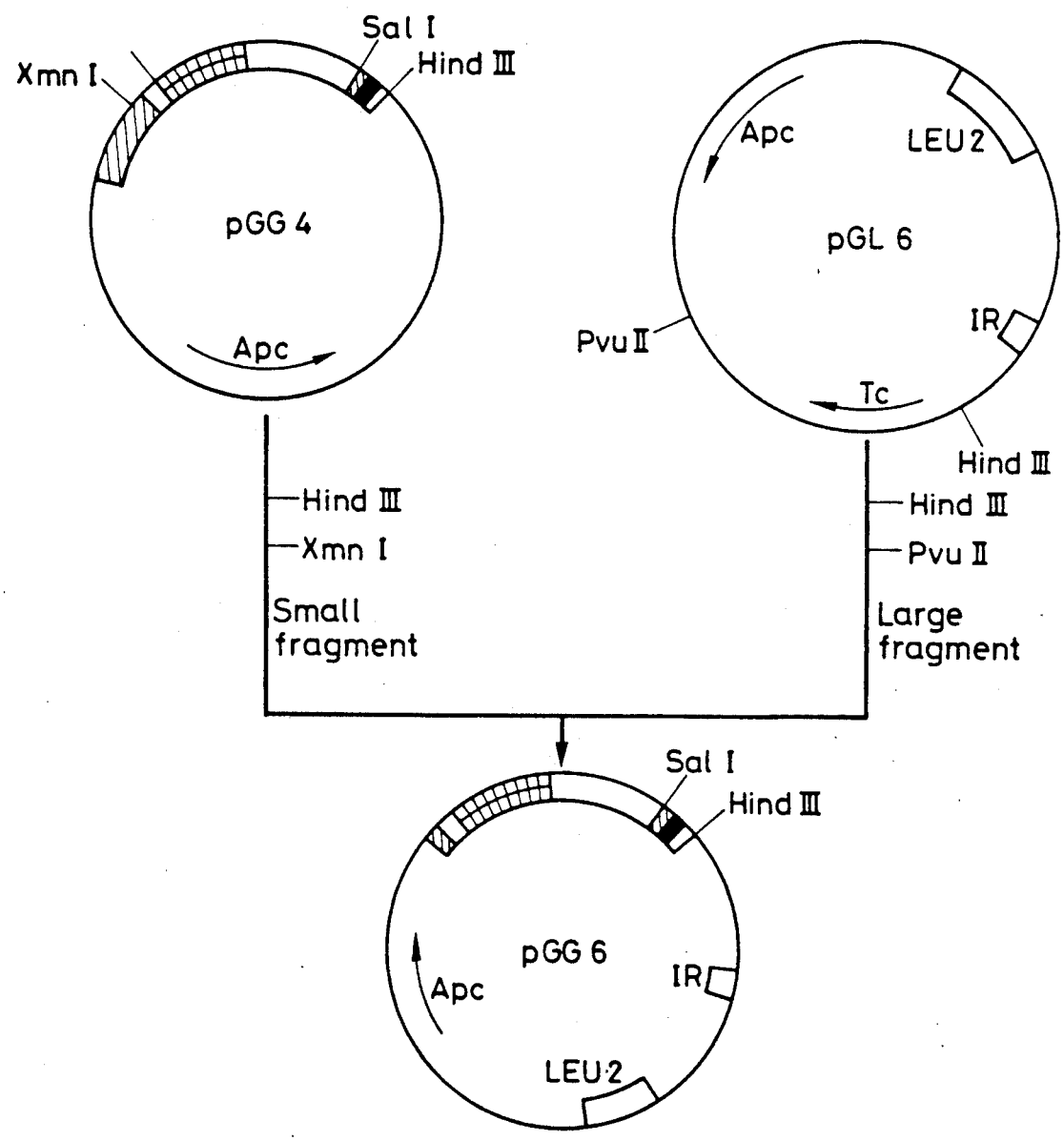
FIG. 4 illustrates the preparation of an HBsAg-producing plasmid carrying thereon the GAP-DH small-sized promoter of the present invention.

Since it was unclear where the promoter of GAP-DH gene existed, the promoter region was successively digested using various restriction enzymes. 2 μg of pGG4 was completely digested with 1U of a restriction enzyme, Xmnl (produced by NEB) and 1U of HindIII, followed by electrophoresis to prepare a 1.8 kB DNA fragment containing the GAP-DH promoter (−165 bp μ), HBsAg gene and GAP terminator. 1 μg of pGL6 was completely digested with 1U of PvuII (produced by Takara Shuzo Co., Ltd.) and 1U of HindIII, followed by electrophoresis to prepare a 5.6 kb DNA fragment. The 1.8 kb DNA fragment and the 5.6 kb DNA fragment were ligated to each other using T4 DNA ligase to obtain a plasmid having the GAP-DH promoter, which was designated as pGG6 (FIG. 4).

Then, Saccharomyces cerevisiae, GRF18 (α, his, leu, trp, met) was transfected with pGG6 and pGG5. The resulting transfected yeast was purified to a leucine-free minimal medium plate comprising 0.7% Yeast Nitrogen Base (Difco), 2% dextrose and 1.5% agar. The resulting pGG5 or pGG6/Saccharomyces cerevisiae, GRF18 of pure line was shake-cultured in a minimal medium having the same composition as used above but containing no agar at 30° C. for 2 days to obtain a seed culture. 80 ml of the same minimal medium was inoculated with 1% seed culture, followed by cultivation at 30° C. for 2 hours. The microbial cells were collected by centrifugation, washed with a physiological saline and suspended in a buffer solution comprising 50 mM of tris-HCl (pH 7.5) and 1 mM of EDTA. The suspension was treated in an ultrasonic wave generator (UR-200P, manufactured by Tomy Seikosha) at level 10 for 9 minutes under ice-cooling, followed by centrifugation at 0° C. at 13,000×g. The resulting supernatant was assayed for HBsAg activity according to an RPHA method using Antihebsel (produced by Green Cross Corporation). The results obtained are shown in the Table below.

TABLE

| Plasmid | Host | HbsAg Activity ($2^n$)* |
|---|---|---|
| pGG5 | Saccharomyces cerevisiae GRF18 | 8 |
| pGG6 | Saccharomyces cerevisiae GRF18 | 8 |

Note:
*means a dilution.

The results shown in the above table indicate that the promoter of this invention maintained a potent promoter activity.

While the invention has been described in detail and with reference to specific embodiments thereof, it will be apparent to one skilled in the art that various changes and modifications can be made therein without departing from the spirit and scope thereof.

What is claimed is:

1. A DNA sequence of the yeast glyceraldehyde-3-phosphate dehydrogenase (GAP-DH) promoter which consists of, as a minimum unit, the region upstream of the initiator codon of the yeast GAP-DH protein of from at least −25 bp up to −164 bp.

2. The DNA sequence as in claim 1, wherein said GAP-DH promoter has the following sequence:

```
        −160                    −140
     TATTCCCCTACTTGACTAATAAGTATA

−130                    −110
     TAAAGACGGTAGGTATTGATTGTAATTC

−100                     −80
     TGTAAATCTATTTCTTAAACTTCTTAAATT

−70                     −50
     CTACTTTTATAGTTAGTCTTTTTTTTAGTT

−40
         TTAAAACACCAAGAACTTAGTTTCG
```

3. The DNA sequence as in claim 1, wherein said yeast GAP-DH promoter is derived from Saccharomyces.

4. A process for preparing a heterologous protein which comprises
   inserting a small-sized GAP-DH promoter containing a DNA sequence in the yeast GAP-DH promoter consisting essentially of, as a minimum unit, the region upstream of the initiation codon of the yeast GAP-DH protein of at least −25 bp up to −164 bp into a plasmid;
   inserting a gene which encodes a useful physiologically active substance downstream of the small-sized GAP-DH promoter in to the plasmid to obtain a recombinant plasmid;

introducing the recombinant plasmid into yeast to transform the yeast and cultivating the transformant to produce a desired protein.

5. The process as in claim 4, wherein said GAP-DH promoter has the following sequence:

```
      -160                    -140
TATTCCCCTACTTGACTAATAAGTATA
      -130                    -110
TATAAAGACGGTAGGTATTGATTGTAATTC
      -100                    -80
TGTAAATCTATTTCTTAAACTTCTTAAATT
      -70                     -50
CTACTTTTATAGTTAGTCTTTTTTTTAGTT
      -40
TTAAAACACCAAGAACTTAGTTTCG
```

6. The process as in claim 4, wherein said yeast GAP-DH promoter is derived from Saccharomyces.

* * * * *